United States Patent [19]

Goldstein et al.

[11] 4,002,740
[45] Jan. 11, 1977

[54] THYMOPOIETIN II AND THERAPEUTIC USE THEREOF

[76] Inventors: Gideon Goldstein, 4421 Douglas Ave., Riverdale, N.Y. 10471; David H. Schlesinger, c/o Mass. Gen. Hospital, Boston, Mass. 02114

[22] Filed: Aug. 21, 1975

[21] Appl. No.: 606,654

[52] U.S. Cl. .................. 424/177; 260/112.5 R; 260/78 A
[51] Int. Cl.² ............. A61K 37/00; C07C 103/52
[58] Field of Search ............ 260/112.5 R, 78 A; 424/177

[56] References Cited

OTHER PUBLICATIONS

Goldstein et al.: Annals N.Y. Acad. Sci., 183, pp. 230–240, (1971).
Goldstein: Nature, 247, 11–14 (1974).

Primary Examiner—Lewis Gotts
Assistant Examiner—Reginald J. Suyat
Attorney, Agent, or Firm—Lowe, King, Price & Markva

[57] ABSTRACT

There is disclosed a tridecapeptide of the following sequence:

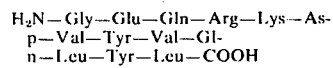

This tridecapeptide has the capability of including the differentiation of T lymphocytes but not of complement receptor ($CR^+$) B lymphocytes and thus is useful in a number of therapeutic areas. Also provided are novel intermediate polypeptides and methods of manufacture of the peptides.

6 Claims, No Drawings

THYMOPOIETIN II AND THERAPEUTIC USE THEREOF

BACKGROUND OF THE INVENTION

1. Field of the Invention

This invention relates generally to new polypeptides, to methods for preparation of the new polypeptides, and fields of use for the polypeptides.

2. Description of the Prior Art

It is well known that many polypeptides have been isolated from various organs or animals. Until about the past decade, however, very little was known about the thymus, an organ which in man comprises about 0.8% of his body weight at birth, although it has been previously hypothesized that a neuromuscular blocking substance existed in the thymus. Despite keen interest in possible functions of the thymus and early speculation and experimentation, little was known of the function of the thymus until recently. It is now realized, however, that the thymus is a compound organ with both epithelial (endocrine) and lymphoid (immunological) components and thus the thymus is involved in the immunity functions of the body. The thymus is known to be a compound organ consisting of an epithelial stroma derived from the third branchial arch and lymphocytes derived from stem cells originating in haemopoietic tissues, Goldstein et al, *The Human Thymus*, Heinemann, London, 1969. Lymphocytes are differentiated within the thymus and leave as mature thymus-derived cells, called T cells, which circulate to the blood, lymph, spleen and lymph nodes. The induction of stem cell differentiation within the thymus appears to be mediated by secretions of the epithelial cells of the thymus but difficulties with bioassays have hindered the complete isolation and structural characterization of any hormones which may be present.

It has been known for some time that the thymus is connected with the immunity characteristics of the body and therefore great interest has been indicated in substances which have been isolated from the thymus. In this regard, there have been published in recent years a relatively large body of articles based on scientific work relating to materials which are present in bovine thymus. In fact, the Applicants have published a number of articles which relate to research in this area. Pertinent publications may be found for example in *The Lancet*, July 20, 1968, pps. 119–122; *Triangle*, Vol. 11, No. 1, pps. 7–14, 1972; *Annals of the New York Academy of Sciences*, Vol. 183, pps. 230–240, 1971; and *Clinical and Experimental Immunology*, Vol. 4, No. 2, pps. 181–189, 1969.

In the article by Goldstein and Manganaro in *Annals of the New York Academy of Sciences*, Vol. 183, pps. 230–240, 1971, there are disclosures regarding the presence of a thymic polypeptide which causes a myasthenic neuromuscular block in animals, which is analogous to the human disease of myasthenia gravis. Further, in this article it was discovered that two distinct effects were caused by separate polypeptides in bovine thymus. One of these polypeptides, named "thymotoxin", was believed to cause myositis but it was further indicated that this polypeptide had not been isolated although it appeared to be a polypeptide of approximately 7,000 molecular weight, had a strong net positive charge and was retained on CM-Sephadex at a pH of 8.0.

In copending application Ser. No. 429,202, filed Dec. 28, 1973, now abandoned, and refiled as Ser. No. 606,843, filed Aug. 23, 1975 of one of the Applicants, and in the publication "Nature", published on Jan. 4, 1974, there are described products identified as Thymin I and Thymin II which are found to be new polypeptides isolated from bovine thymus which have particular uses in various therapeutic areas. Because of the use of similar names for other products isolated from the thymus in the prior art, these Thymin I and Thymin II products are now named as Thymopoietin I and Thymopoietin II.

The present invention provides a synthesized polypeptide of definite sequence which has been found to exhibit many of the characteristics of the long chain polypeptide isolated and named as Thymopoietin II in the above publications and copending patent application Ser. No. 429,202.

SUMMARY OF THE INVENTION

It is accordingly one object of this invention to provide a new polypeptide which is important biologically.

A further object of the invention is to provide a new polypeptide which has the ability in nanogram concentrations to induce differentiation of bone marrow cells to T cells thus giving rise to thymus-derived lymphocytes and thereby being highly useful in the immunity system of humans and animals.

A further object of the invention is to provide novel intermediate products, methods for synthesizing the novel polypeptide of this invention, as well as compositions and methods for its use in biological actions.

Other objects and advantages of the invention will become apparent as the description thereof proceeds.

In satisfaction of the foregoing objects and advantages there is provided by this invention a novel polypeptide of the following sequence:

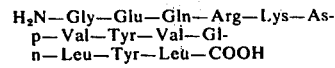

There is also provided a novel peptide-resin intermediate formed in the preparation of the polypeptide of this invention which intermediate has the following general sequence:

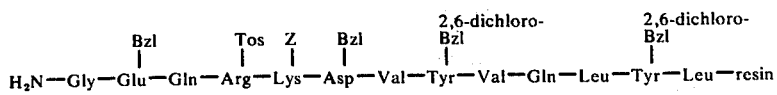

as well as this peptide freed from the resin, wherein Bzl represents a benzyl protective group on the amino acids indicated, Tos is a tosyl protective group, Z is a benzyloxycarbonyl protective group, and the resin is a solid phase polymer which acts as a support for the reaction. Also provided as a procedure for preparation of the polypeptide of the invention by solid phase peptide synthesis, as well as therapeutic compositions containing the polypeptide, and methods for administration of the polypeptides to humans and animals for effecting biological actions on the hosts.

DESCRIPTION OF PREFERRED EMBODIMENTS

As indicated above, this invention is concerned with a new polypeptide having therapeutic value in various areas, intermediates formed in the preparation of this polypeptide, therapeutic compositions and methods for their use utilizing the polypeptide of this invention, and methods for manufacture of the polypeptide. As indicated, the polypeptide of this invention is a tridecapeptide of the following sequence:

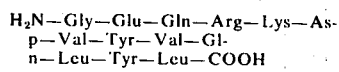

H₂N—Gly—Glu—Gln—Arg—Lys—Asp—Val—Tyr—Val—Gln—Leu—Tyr—Leu—COOH

In the above structure the amino acid components of the peptide are identified by abbreviations for convenience. These abbreviations are as follows:

| Amino Acid | Abbreviated Designation |
|---|---|
| Glycine | Gly |
| L-glutamic acid | Glu |
| L-glutamine | Gln |
| L-arginine | Arg |
| L-lysine | Lys |
| L-aspartic acid | Asp |
| L-valine | Val |
| L-tyrosine | Tyr |
| L-leucine | Leu |

The polypeptide of this invention is a 13 amino acid tridecapeptide which has been found to exhibit characteristics similar to a 49 amino acid polypeptide isolated from bovine thymus and indicated previously in copending application Ser. No. 429,202, as being Thymin II, now called Thymopoietin II. It is particularly characterized in its ability to induce the selective differentiation of Thy-1⁺ T cells in concentrations of 1 ng to 1 µg/ml, but does not induce the differentiation of CR⁺ B cells in concentrations from 0.01 ng to 10 µg/ml.

Studies of this synthetic peptide in the induction assay in vitro showed it to have the same induction specificity as thymopoietin II. That is, it induced the differentiation of Thy-1 cells to Thy-1⁺ T cells, but did not induce the differentiation of CR⁻ cells to CR⁺ B cells. While many substances have been identified that can mimic thymopoietin in vitro and induce T cell differentiation by raising intracellular cyclic AMP, it is emphasized that few substances are active at such low concentration, and that thymopoietin alone, of all substances tested, is selective in inducing T cell differentiation but not CR⁺ B cell differentiation.

Because of these characteristics of the polypeptide of this invention, it is therapeutically useful in the treatment of humans and animals since it has the capability for inducing the differentiation of lymphopoietic stem cells originating in the hemopoietic tissues to mature thymus derived cells or T cells which are capable of involvement in the immune response to the body. As a result the product of this invention is considered to have multiple therapeutic uses. Primarily, since the compound has the capability of carrying out certain of the indicated functions of the thymus, it has application in various thymic function and immunity areas. A primary field of application is in the treatment of DiGeorge Syndrome, a condition in which there is a congenital absence of thymus. Injection of the polypeptide will overcome this deficiency. Because of its biological characteristics, which are extremely active at low concentrations, it is considered useful in assisting the collective immunity of the body in that the polypeptide will increase or assist in therapeutic stimulation of cellular immunity and thereby become useful in the treatment of diseases involving chronic infection in vivo, such as fungal or mycoplasma infections, tuberculosis, leprosy, acute and chronic viral infections and the like. Further, the compound is considered to be useful in any area in which cellular immunity is an issue and particularly where there are deficiencies in immunity such as in the DiGeorge Syndrome mentioned above. Also where there is an excess of antibody production due to unbalanced T cells and B cells, the compound can correct this condition by stimulating T cell production. Thus, it may be of therapeutic use in certain autoimmune diseases in which damaging antibodies are present, for example, systemic lupus erythematosus. Further, because of the characteristics of the polypeptide it has in vitro usefulness in inducing the development of surface antigens of T cells, in inducing the development of the functional capacity to achieve responsiveness to mitogens and antigens and cell collaborativity in enhancing the ability of B cells to produce antibodies. The polypeptide is also useful in inhibiting the uncontrolled proliferation of thymin-responsive lymphocytes.

An important characteristic of the polypeptide is its in vivo ability to restore cells with the characteristic of the T cells. Therefore, the polypeptide of this invention is active in many areas as a result of its ability to enhance the immune response in the body.

A further important characteristic of the polypeptide of this invention is that it is highly active in very low concentrations. Thus, it has been found that the polypeptide is active in concentrations ranging from 1 nanogram per ml, and is maximally active at concentrations from about 100 nanogram per ml. The carrier may be any of the well known carriers for this purpose including normal saline solutions, preferably with a protein diluent such as bovine serum albumin to prevent adsorptive losses to glassware at these low concentrations. The polypeptide is therapeutically active at a range of above about 1 mg/kg of body weight of the host.

The polypeptide of this invention was prepared by using the concepts of the method of Merrifield as reported in *Journal of American Chemical Society*, 85, pps. 2149–2154, 1963. The synthesis involved the stepwise addition of protected amino acids to a growing peptide chain which was bound by covalent bonds to a solid resin particle. By this procedure, reagents and by-products were removed by filtration and the recrystallization of intermediates were eliminated. The general concept of this method depends on attachment of the first amino acid of the chain to a solid polymer by a covalent bond and the addition of the succeeding amino acids one at a time in a stepwise manner until the desired sequence is assembled. Finally the peptide is removed from the solid support and protective groups removed. This method provides a growing peptide chain attached to a completely insoluble solid particle so that it is in a convenient form to be filtered and washed free of reagents and by-products. The amino acids may be attached to any suitable polymer which merely has to be insoluble in the solvents used and have a stable physical form permitting ready filtration. It must contain a functional group to which the first protected amino acid can be firmly linked by a covalent bond. Various polymers are suitable for this purpose such as cellulose, polyvinyl alcohol, polymethacrylate and sulfonated polystyrene but in the synthesis of this invention, there was used a chloromethylated copolymer of styrene and divinylbenzene.

The various functional groups on the amino acids which were active but which were not to enter into the reactions were protected by conventional protecting groups as used in the polypeptide art. Thus, the amino group on glutamine, asparagine and tyrosine was protected by a benzyl group (Bzl), the amino group on the side-chain of the arginine amino acid was protected by tosyl (Tos) and the active amino group on lysyl was protected by benzyloxycarbonyl (Z). In general, the synthesis was performed by a modification of this method in that fluorescamine was used to determine if coupling was complete by an indication of positive fluorescence (see Felix et al, Analyt, Biochem., 52, 377, 1973). If complete coupling was not indicated, the coupling was repeated with the same protected amino acid before deprotection.

The general procedure involved initially esterifying α-butyloxycarbonyl L-leucine to chloromethylated resin in absolute alcohol containing an amine. The coupled amino acid resin was then filtered, washed with alcohol and dried. The other amino acids were similarly coupled. At the conclusion of the coupling reactions the following protected tridecapeptide resin had been synthesized.

Alpha-BOC-glycine
Alpha-BOC-O-benzyl-L-glutamic acid
Alpha-BOC-L-Glutamine-O-nitrophenyl ester
Alpha-AOC-Ng-Tos-L-arginine
Alpha-BOC-O-benzyl-L-aspartic acid
Alpha-BOC-L-valine
Alpha-BOC-L-leucine.½ H₂O
Alpha-BOC-2,6-dichlorobenzyl-L-tyrosine
Alpha-BOC-2-chloro-benzyloxycarbonyl-L-lysine In these reagents, BOC is butyloxycarbonyl and Tos is tosyl. "Sequenal" grade reagents for amino acid sequence determinations, dicyclohexyl carbodiimide, fluorescamine, and the resin were also purchased commercially. The resin used was a styrene divinyl benzene resin, 200–400 mesh size containing 1% divinyl benzene and 0.75 mM of chloride per gram of resin.

In preparation of the polypeptide, 2mM of α-BOC-L-leucine were esterified to 2mM chloromethylated resin in absolute alcohol containing 1mM of triethylamine for 24 hours at 80° C. The resulting coupled amino acid resin was filtered, washed with absolute alcohol and dried. Thereafter, the α-BOC or α-AOC amino acids were similarly coupled to the deprotected α-amino group of the peptideresin in the correct sequence to result in the polypeptide of this invention using equivalent amounts of dicyclohexyl carbodiimide except for α-BOC-L-glutamine-O-nitrophenol ester which was coupled directly. After each coupling reaction, an ali-

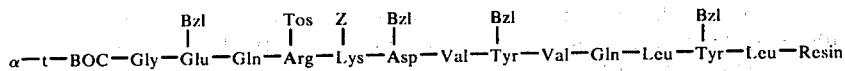

In the above intermediate tridecapeptide resin, it will be noted that the expression Bzl stands for benzyl, Tos stands for tosyl, Z stands for benzyloxycarbonyl. The resin is any of the resins mentioned above as being useful in the process.

quot of resin was tested with fluoroescamine and if positive fluorescence was found, coupling was taken to be incomplete and was repeated with the same protective amino acid. As a result of the several coupling reactions, the following tridecapeptide-resin resulted:

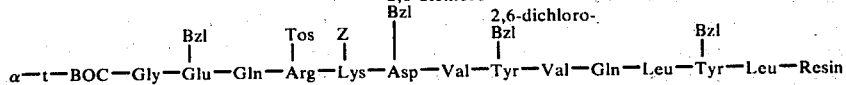

The peptide-resin was then treated with trifluoroacetic acid to provide an intermediate tridecapeptide of the following sequence:

This peptide-resin was cleaved and the protective groups removed in a Kel cleavage apparatus (Peninsula Laboratories, Inc.) using anhydrous hydrogen fluoride

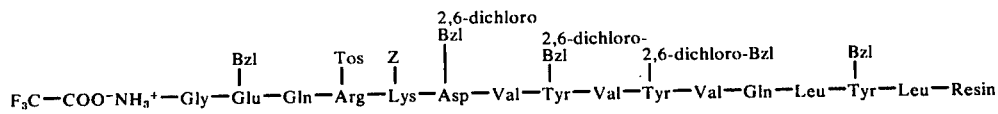

wherein Bzl, Tos and Z are as indicated above. The protective groups were then removed by conventional means using anhydrous hydrogen fluoride and the peptide was recovered.

The following examples are presented to illustrate the invention but it is not to be considered as limited thereto. In the Examples and throughout the specification, parts are by weight unless otherwise indicated.

EXAMPLE I

In preparation of the polypeptide of this invention the following materials were purchased commercially.

at 0° C. for 60 minutes with 1.2 ml anisole per gram peptide-resin as scavenger. The peptide resin mixture was lyophilized and washed with anhydrous ether and the peptide extracted with glacial acetic acid and water. The peptide was chromatographed on P-6 Bio-Gel in 1 N acetic acid and carboxymethycellulose-urea and then desalted. The resulting polypeptide was determined to be 94% pure and was determined to have the following sequence:

H₂N—Gly—Glu—Gln—Arg—Lys—Asp—Val—Tyr—Val—Gln—Leu—Tyr—Leu—COOH

EXAMPLE II

To determine the activity and characteristics of the polypeptide, determinations were carried out on healthy 5–6 week old nu/nu mice of both sexes, the mice being bred on a BALB/c background (thymocytes expressing Thy-1.2 surface antigen) and maintained under conventional conditions. For the antisera, anti Thy-1.2 sera were prepared in Thy-1 congenic mice.

For the induction of in vitro of Thy-1⁺ T cell or CR⁺ B cell differentiation, the induction of thymocyte differentiation from prothymocytes in vitro was performed as described by Komuro and Boyse, (*Lancet* 1, 740, 1973), using the acquisition of Thy-1.2 as a marker of T cell differentiation. The induction of CR⁺ B cell differentiation from CR⁻ B cell precursors in vitro was performed under similar conditions using as the assay criterion, the capacity of CR⁺ B cells to bind sheep erythrocytes coated with subagglutinating quantities of rabbit antibody and nonlytic complement. Spleen cell populations from healthy nu/nu mice fractionated on discontinuous bovine serum albumin gradients were used as the source of both precursor types (Thy-1 and CR⁺) because they have few or no Thy-1⁺ cells and low numbers of CR⁺ cells.

As a result of this determination it was found that the polypeptide displayed a selectivity of actions similarly to that of Thymopoietin II in inducing the differentiation of T-lymphocytes but not of complement receptors (CR+) B-lymphocytes. The tridecapeptide induced differentiation of Thy-1⁺ T cells in concentrations ranging from 1 ng to 1 µg/ml. It did not induce the differentiation of CR⁺ B cells in concentrations of 0.01 ng to 10 µg/ml.

The invention has been described herein with reference to certain preferred embodiments. However, as obvious variations will appear to those skilled in the art, the invention is not to be considered as limited thereto.

What is claimed is:

1. A polypeptide of the following sequence:

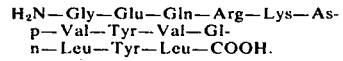

2. An intermediate polypeptide of the following sequence:

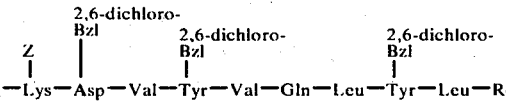

wherein Bzl is benzyl, Tos is tosyl and Z is benzyloxycarbonyl.

3. An intermediate polypeptide of the following sequence:

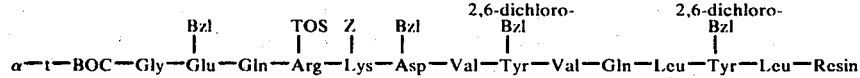
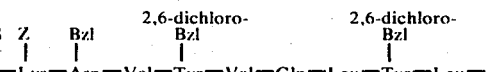

wherein Bzl is benzyl, TOS is tosyl, Z is benzyloxycarbonyl, t-BOC is t-butyloxycarbonyl, and the resin is an insoluble polymer having a stable physical form and attached to the adjacent amino acid by covalent bonds.

4. A therapeutic composition of matter comprising a therapeutically effective amount of the composition of claim 1 in a pharmaceutically acceptable carrier.

5. A therapeutic composition of matter according to claim 4 wherein the therapeutically effective amount of the polypeptide is at least about 1 mg/kg of body weight.

6. A method for the treatment of conditions selected from the group consisting of DiGeorge Syndrome, fungal infections, mycoplasma infections, tuberculosis, leprosy, acute and chronic viral infections and systemic lumpus erythemotosus, said conditions resulting from relative or absolute T-cell deficiencies, which comprises the administration of a composition of claim 4 by injection.

* * * * *

UNITED STATES PATENT OFFICE
CERTIFICATE OF CORRECTION

PATENT NO. : 4,002,740
DATED : January 11, 1977
INVENTOR(S) : Goldstein and Schlesinger It is certified that error appears in the above-identified patent and that said Letters Patent are hereby corrected as shown below:

In the Title of the Patent, "Thymopoietin II and Therapeutic Use Thereof" should be --TRIDECAPEPTIDE COMPOSITIONS AND METHODS--

Signed and Sealed this

Seventeenth Day of January 1978

[SEAL]

Attest:

RUTH C. MASON
Attesting Officer

LUTRELLE F. PARKER
Acting Commissioner of Patents and Trademark